US012778416B2

(12) United States Patent
Barraza-Bernal et al.

(10) Patent No.: US 12,778,416 B2
(45) Date of Patent: Nov. 3, 2026

(54) DEVICES AND METHODS FOR DETERMINING DATA RELATED TO A PROGRESSION OF REFRACTIVE VALUES OF A PERSON

(71) Applicants: Carl Zeiss Vision International GmbH, Aalen (DE); Carl Zeiss Shanghai Co. Ltd., Shanghai (CN)

(72) Inventors: Maria Jose Barraza-Bernal, Aalen (DE); Arne Ohlendorf, Tübingen (DE); Pablo Sanz Diez, Tübingen (DE); Xiancai Feng, Shanghai (CN); Siegfried Wahl, Donzdorf (DE); Timo Kratzer, Aalen (DE)

(73) Assignees: Carl Zeiss Vision International GmbH, Aalen (DE); Carl Zeiss Shanghai Co. Ltd., Shanghai (CN)

(*) Notice: Subject to any disclaimer, the term of this patent is extended or adjusted under 35 U.S.C. 154(b) by 295 days.

(21) Appl. No.: 18/640,171

(22) Filed: Apr. 19, 2024

(65) Prior Publication Data

US 2024/0260827 A1 Aug. 8, 2024

Related U.S. Application Data

(63) Continuation of application No. PCT/EP2022/080784, filed on Nov. 4, 2022.

(30) Foreign Application Priority Data

Nov. 5, 2021 (WO) ................ PCT/CN2021/128940

(51) Int. Cl.
*A61B 3/103* (2006.01)
*A61B 3/028* (2006.01)
(Continued)

(52) U.S. Cl.
CPC .............. *A61B 3/103* (2013.01); *A61B 3/028* (2013.01); *A61B 5/4842* (2013.01); *G16H 10/60* (2018.01); *G16H 50/30* (2018.01); *G16H 50/50* (2018.01)

(58) Field of Classification Search
CPC ....... A61B 3/103; A61B 3/028; A61B 5/4842; G16H 10/60; G16H 50/30; G16H 50/50;
(Continued)

(56) References Cited

U.S. PATENT DOCUMENTS

2018/0160894 A1 6/2018 Gupta et al.
2019/0258930 A1 8/2019 Ohlendorf et al.
(Continued)

FOREIGN PATENT DOCUMENTS

AU 2018202725 A1 11/2018
CN 104751611 A 7/2015
(Continued)

OTHER PUBLICATIONS

Office Action of the Japanese Patent Office (JPO) issued in JP 2024-527065, which is a counterpart hereof, mailed on May 27, 2025 and English-language machine translation thereof.
(Continued)

*Primary Examiner* — Mohammed A Hasan
(74) *Attorney, Agent, or Firm* — Qubit IP, PLLC

(57) ABSTRACT

A processing device, a computer-implemented method, and a computer program for determining data related to a progression of refractive values of a person; and a system, a computer-implemented method, and a computer program for providing data related to a progression of refractive values are disclosed. The processing device receives data related to a person, including a refractive status of the person; age, gender, and ethnicity of the person; and a risk factor related to the person; and determines data related to
(Continued)

the progression of refractive values deploying a machine learning algorithm, wherein the machine learning algorithm includes at least one prediction model for determining a relationship between the data related to the person and the progression of the refractive values of the person. By using the processing device, the system, the computer-implemented methods, and the computer programs the prediction of both myopia onset and myopia progression can be improved.

25 Claims, 2 Drawing Sheets

(51) Int. Cl.

*A61B 5/00* (2006.01)
*G16H 10/60* (2018.01)
*G16H 50/30* (2018.01)
*G16H 50/50* (2018.01)

(58) Field of Classification Search

CPC ........ G16H 50/20; G16H 50/70; G06N 20/10; G06N 20/20
USPC .......................................................... 351/205
See application file for complete search history.

(56) References Cited

U.S. PATENT DOCUMENTS

| | | | | |
|---|---|---|---|---|
| 2019/0272922 | A1* | 9/2019 | Albright | G16H 50/70 |
| 2020/0381096 | A1* | 12/2020 | Zaharchuk | G06V 10/774 |
| 2021/0145271 | A1 | 5/2021 | Zimmerman | |
| 2021/0290077 | A1 | 9/2021 | Lee et al. | |
| 2021/0375460 | A1* | 12/2021 | Li | A61B 3/00 |
| 2022/0028552 | A1 | 1/2022 | Drobe et al. | |
| 2022/0165418 | A1* | 5/2022 | Li | G06V 10/7747 |
| 2023/0035564 | A1* | 2/2023 | Dong | G16H 50/20 |

FOREIGN PATENT DOCUMENTS

| | | | | |
|---|---|---|---|---|
| CN | 106980748 | A | 7/2017 | |
| CN | 107358036 | A | 11/2017 | |
| CN | 110288266 | A | 9/2019 | |
| CN | 110299204 | A | 10/2019 | |
| CN | 112289446 | A | 1/2021 | |
| CN | 113261067 | A | 8/2021 | |
| JP | 2019533516 | A | 11/2019 | |
| KR | 20180119505 | A | 11/2018 | |
| KR | 20200077085 | A | 6/2020 | |
| KR | 20210088654 | A | 7/2021 | |
| WO | WO-2020083382 | A1 * | 4/2020 | G06Q 10/04 |
| WO | 2020126514 | A1 | 6/2020 | |
| WO | WO-2020126513 | A1 * | 6/2020 | G16H 50/70 |

OTHER PUBLICATIONS

Decision to grant of the Japanese Patent Office (JPO) issued in JP 2024-527065, which is a counterpart hereof, mailed on Aug. 19, 2025 and English-language machine translation thereof.

Pascolini et al., “Global estimates of visual impairment,” Ophthalmol, vol. 96, pp. 614 to 618, Dec. 1, 2011.

French et al., “Time outdoors and the prevention of myopia,” Experimental Eye Research, vol. 114, pp. 58 to 68, May 2, 2013.

Industrial Norm “Ophthalmic optics—Spectacle lenses—Vocabulary (ISO 13666:2019),” English version EN ISO 13666:2019, Dec. 2019.

Walline et al., “Interventions to slow progression of myopia in children,” Cochrane Database Syst Rev., vol. 1, retrieved from the internet URL: https://doi.org/10.1002/14651858.CD004916.pub4, Jan. 13, 2020.

Grzybowski et al., “A review on the epidemiology of myopia in school children worldwide,” BMC Ophthalmology , vol. 20, Art. 27, 2020.

Morgan et al., “IMI Risk Factors for Myopia,” IOVS, Special Issue, vol. 62, No. 5, Art. 3, Apr. 28, 2021.

Homepage of Brien Holden Vision Instiitute, Myopia Calculator, available at the URL: https://bhvi.org/myopia-calculator-resources/ (last accessed Apr. 11, 2024).

Homepage of Eyetific Sarl, Myoopia Calculators, available at URL: https://myopiacare.com/myappia-myocalc/ (last accessed Apr. 11, 2024).

Written opinion issued in PCT/EP2022/080784, to which this application claims priority, mailed Jan. 30, 2024.

International Preliminary Report on Patentability issued in PCT/EP2022/080784, to which this application claims priority, mailed Jan. 30, 2024.

Dong et al., “Prevalence and time trends of myopia in children and adolescents in China,” Retina, vol. 40, No. 3, pp. 399 to 411, 2019.

Tang et al. “A machine learning-based algorithm used to estimate the physiological elongation of ocular axial length in myopic children,” Eye and Vision (2020) 7:50, published online Oct. 22, 2020.

Office action by the Indian Patent Office issued in application No. 202417037881, which is a counterpart hereof, dated Jan. 23, 2026 (in Hindi and English).

Office Action by the Korean Patent Office (KIPO), issued in KR 10-2024-7014901, which is a counterpart hereof, mailed on Apr. 30, 2026, and English-language translation thereof.

* cited by examiner

DEVICES AND METHODS FOR DETERMINING DATA RELATED TO A PROGRESSION OF REFRACTIVE VALUES OF A PERSON

CROSS REFERENCE TO RELATED APPLICATIONS

This application is a continuation application of international patent application PCT/EP2022/080784, filed on Nov. 4, 2022 and designating the U.S., which claims priority to international patent application PCT/CN2021/128940, filed on Nov. 5, 2021, both of which are hereby incorporated by reference in their entireties.

TECHNICAL FIELD

The present disclosure relates to a processing device, a computer-implemented method and a computer program for determining data related to a progression of refractive values of a person and to a system, a computer-implemented method and a computer program for providing data related to a progression of refractive values.

BACKGROUND

Pascolini D. & Mariotti S. P, "Global estimates of visual impairment," 2010, Br J Ophthalmol 2012; 96:614e618. doi:10.1136/bjophthalmol-2011-300539, describe visual impairments as a global health and socioeconomic issue, characterized by an uneven distribution. A major cause of visual impairments are uncorrected refractive errors, covering 43% of the causes. Despite the emergence of preventive policies, the situation has not changed much in the last 10 years and uncorrected refractive error still shows up on the lists of major causes for visual impairments in different areas of the globe.

Grzybowski A., et al., "A review on the epidemiology of myopia in school children worldwide," BMC Ophthalmology (2020) 20:27, point out a myopia prevalence of 60% in Asiatic countries, wherein East Asiatic countries show an even higher prevalence of 73%. Further, the study shows a myopia prevalence of 40% in European countries and of 42% in North American children. On the contrary, African and South American countries show myopia prevalence under 10%.

Dong L., et al., "Prevalence and time trends of myopia in children and adolescents in China," Retina 40(3); 2019, pp-399-411, describe a recent meta-analysis on the prevalence and myopia trends in Chinese children and adolescents estimating that in 3 decades the prevalence of myopia might reach 84%.

Considering the visual and pathological consequences of myopia and high myopia, it is important to address this problem at early stages. Standard methods for correcting refractive errors such as myopia are spectacles, contact lenses or refractive surgery. However, based on the current and projected estimations on refractive errors worldwide, these methods only correct the error but may not be sufficient to reduce the further progression.

Besides these mentioned correcting methods, Walline J. J., et al., "Interventions to slow progression of myopia in children," 2020, Cochrane Database Syst Rev. 1: CD004916; doi.org/10.1002/14651858.CD004916.pub4, demonstrate that different solutions have proven successful to slow or stop the rate of myopia progression. Examples include an implementation of different doses of atropine; a use of spectacles lenses, specifically bifocal spectacles, progressive addition lenses, peripheral defocus or defocus incorporated multiple segments lenses; a use of Multifocal contact lenses; and a use of orthokeratology.

Whether a type of myopia treatment may be applied to the person or not, mainly depends on a risk for the person to develop myopia and for myopia to progress. Morgan I. G., et al., "IMI Risk Factors for Myopia," Invest. Ophthalmol. Vis. Sci. 2021; 62(5): 3 report that the myopia community has invested a lot of effort during the last decades on understanding what are crucial parameters capable of influencing this risk. Although a wide number of variables influencing onset and progression of myopia has been suggested, only a handful of them are frequently named. Among these parameters are ethnicity, behavior, and parental myopia.

Myopia Calculator, available via the url bhvi.org/myopia-calculator-resources/provides an online software for predicting a progression of refractive values of a person by using data related to the person, comprising age, ethnicity, and refractive error of the person and a recommended myopia treatment to be applied to the person. Based hereon, the software calculates predicted values for a percentage of reduction of the progression of myopia compared to a standard correction procedure, such as single vison spectacle lenses, and for a course of the refractive error of the person if the recommended myopia treatment is commenced immediately or not.

MyAppia, available via the url myopiacare.com/myappia-myocalc/provides a further online software for predicting the progression of refractive values of a person by using data related to the person, comprising age; a refractive status of the person comprising a spherical equivalent of an eye of the person, and one or more recommended myopia treatments to be applied to the person. Based hereon, the software calculates predicted values for the percentage of reduction of the progression of myopia and for the course the refractive error of the person both based on one or more of the recommended type of myopia treatments to be applied to the person.

U.S. 2018/160894 A1 discloses methods, systems, and computer program products for forecasting eye condition progression for eye patients. When a patient visits an eye practitioner, the patient or a guardian may be interested in the current eye condition as well as a prediction of eye condition progression in the future. Aspects of the disclosure can be used to predict the progress of an eye condition for a patient, e.g., a child, at a number of different post-examination times after an examination. Predicting the progress of an eye condition for a patient over time can be used to assist the eye practitioner in tailoring a treatment plan and/or tailoring a subsequent examination schedule for the patient.

WO 2020/083382 A1 discloses systems, methods, devices, and media for carrying out diagnosis of myopia onset and progression. Machine learning algorithms enable the automated analysis of relevant features to generate predictions. Also disclosed are treatment methods incorporating the machine learning algorithms to identify suitable treatments and predict treatment efficacy.

WO 2020/126513 A1 discloses a method for building a prediction model for predicting evolution over time of at least one vision-related parameter of at least one person, which comprises: obtaining successive values respectively corresponding to repeated measurements over time of at least one parameter of a first predetermined type for at least one member of a group of individuals; obtaining evolution over time of the vision-related parameter(s) for the member(s) of the group of individuals; building by at least one processor the prediction model, including associating at least part of the successive values with the obtained evolution over time of the vision-related parameter(s) for the member(s) of the group of individuals, the associating including jointly processing the at least part of the successive values associated with a same one of the parameter(s) of the first predetermined type. The prediction model depends differentially on each of the jointly processed values.

WO 2020/126514 A1 discloses a method for predicting evolution over time of at least one vision-related parameter of at least one person comprises: obtaining successive values for the person, respectively corresponding to repeated measurements over time of at least one parameter of a first predetermined type for the person; predicting by at least one processor the evolution over time of the vision-related parameter of the person from the obtained successive values for the person, by using a prediction model associated with a group of individuals; the predicting including associating at least part of the successive values for the person with the predicted evolution over time of the vision-related parameter of the person, the associating including jointly processing the successive values associated with the same parameter of the first predetermined type. The predicted evolution depends differentially on each of the jointly processed values.

U.S. 2021/145271 A1 discloses a system and a method for determining a patient's prescription for corrective lenses using predictive calculations and corrected-eyesight simulation. Together, these technologies act as a digital substitute for phoropter testing, thus reducing the cost, time, and human error associated with an eye exam. Based on age, gender, autorefractor readings, and environmental factors, a patient specific model is calculated and fed into a visual simulation tool. From this simulation, an eye care professional is able to determine the patient's corrective lens prescription.

CN 104751611 A discloses a method, a device and equipment for preventing and controlling myopia. The method includes acquiring data information of user eyesight influence factors; processing the data information of the user eyesight influence factors to obtain parameter values which reflect eye using conditions of users; generating alarms when the parameter values meet preset threshold value conditions.

CN 106980748 A discloses a big data fitting-based method and system for monitoring refractive growth of teenagers. The method comprises building a big data model of a multi-factor dynamic refractive value; and fitting out a dynamic refractive value of a tester by utilizing the big data model of the multi-factor dynamic refractive value in combination with basic information of the tester according to a naked eye vision detection value of the tester, obtaining reasons of poor vision of the tester, and if the tester needs to be subjected to deep refractive growth monitoring, fitting out a static refractive value of the tester by utilizing the big data model and performing long-term monitoring.

CN 107358036 A discloses a method, a device and a system for predicting a myopia risk in children. The method comprises the following steps: acquiring current detection data and a physiological index value of the vision of a user; and according to the current detection data and/or the physiological index value, predicting the myopia risk of the user by using a vision prediction model. According to the method, the myopia risk of the user can be predicted by acquiring the current detection data and the physiological index value of the vision of the user, and adopting the vision prediction model according to the current detection data and/or the physiological index value, so that the user and parents of the user can understand the myopia risk of the user in time, and prevent or treat the myopia in advance.

CN 110288266 A discloses a shortsightedness risk assessment method and system. The method comprises the following steps: acquiring factor data of myopia risk factors of a myopia risk assessment target, wherein the myopia risk factors comprise at least one factor; assigning each myopia risk factor according to the factor data to obtain an assignment result; according to the assignment results of all the myopia risk factors, calculating to obtain a myopia risk index; and obtaining a myopia risk result of the myopia risk assessment target according to the myopia risk index.

CN 110299204 A discloses a myopia prevention and control effect prediction method and system. The method comprises the steps: acquiring a myopia risk index value and a myopia prevention and control index value of a myopia prevention and control target, wherein the myopia risk index value is used for representing the myopia risk degree of a myopia prevention and control target, and the myopia prevention and control index value is used for representing the prevention and control strength of a myopia prevention and control strategy of the myopia prevention and control target; according to the myopia risk index value and the myopia prevention and control index value, performing calculating to obtain a myopia prevention and control efficacy value; and performing prediction to obtain a myopia prevention and control effect of the myopia prevention and control target according to the myopia prevention and control efficacy value.

CN 112289446 A discloses a computer system for predicting juvenile myopia. The computer system comprises a database device, a data input device, a myopia prediction device and a prediction result output device. The myopia prediction device is respectively connected with the database device and the data input device, generates a prediction model by utilizing a tree regression algorithm based on characteristic data of a database in the database device, outputs predicted spherical lens power by utilizing the prediction model based on the characteristic data of a subject, and further outputs a prediction result through a prediction result output device.

KR 2021 0088654 A and U.S. 2022/0028552 A1 disclose a method for building a prediction model for predicting evolution over time of at least one vision-related parameter of at least one person, including: obtaining successive values respectively corresponding to repeated measurements over time of at least one parameter of a first predetermined type for at least one member of a group of individuals; obtaining evolution over time of the vision-related parameter(s) for the member(s) of the group of individuals; building by at least one processor the prediction model, including associating at least part of the successive values with the obtained evolution over time of the vision-related parameter(s) for the member(s) of the group of individuals, the associating including jointly processing the at least part of the successive values associated with a same one of the parameter(s) of the first predetermined type. The prediction model depends differentially on each of the jointly processed values.

In particular with respect to the disclosure of KR 2021 0088654 A or U.S. 2022/0028552 A1, it is therefore an objective of the present disclosure to provide a processing device, a computer-implemented method, and a computer program for determining data related to a progression of refractive values of a person as well as a system, a computer-implemented method, and a computer program for providing data related to a progression of refractive values, which at least partially overcome the limitations of the related art.

It is a particular objective of the present disclosure to provide a processing device, a system, computer-implemented methods and computer programs which are capable of improving a prediction of both myopia onset and myopia progression and which can be used in a more reliable fashion by eye care professionals, such as opticians, optometrists, or ophthalmologists; or by end consumers, such as the person subject to myopia or to a related person, especially a parent of the person or a nurse caring for the person.

SUMMARY

This problem is solved by a processing device, a computer-implemented method and a computer program for determining data related to a progression of refractive values of a person and a system, a computer-implemented method and a computer program for providing data related to a progression of refractive values. Exemplary embodiments, which can be implemented in an isolated fashion or in any arbitrary combination, are listed in the following description.

In a first aspect, the present disclosure relates to a processing device for determining data related to a progression of refractive values of a person. According to the present disclosure, the processing device is configured to

- receive data related to a person, comprising
  - a refractive status of the person;
  - age, gender and ethnicity of the person; and
  - at least one risk factor related to the person;
- determine data related to a progression of refractive values of the person using at least one machine learning algorithm, wherein the at least one machine learning algorithm comprises at least one prediction model for determining a relationship between the data related to the person and the progression of the refractive values of the person.

As used herein, the term "processing" or any grammatical variation thereof refers to applying at least one algorithm to data as received by at least one input file in a fashion that desired data related to a progression of refractive values of the person are provided by at least one output file for further processing. As generally used, the term "data" refers to at least one piece of information as comprised by at least one file, specifically by at least one input file or at least one output file. With particular regard to the present disclosure, the at least one piece of information as comprised by at least one input file may be related to a person while the at least one piece of information as comprised by at least one output file may be related to a progression of refractive values of the person. The at least one algorithm may be configured to determine the data related to the progression of the refractive values of the person from the data related to the person by using the data from the at least one input file according to a predefined scheme, wherein, as described below in more detail, artificial intelligence, in particular at least one machine learning algorithm, may also be applied.

As generally used, the term "processing device" refers to an apparatus which is designated for determining data related to a progression of refractive values of a person from data related to the person as received from at least one input file, which may, typically, be provided to the processing device by at least one input interface, and to provide the data related to the progression of the refractive values of the person, such as for further processing, typically by at least one output interface, in particular by using a system as described below in more detail. Specifically, the processing device may comprise at least one of an integrated circuit, in particular an application-specific integrated circuit (ASIC), or a digital processing device, in particular at least one of a digital signal processor (DSP), a field programmable gate array (FPGA), a microcontroller, a microcomputer, a computer, or an electronic communication unit, specifically a smartphone, a tablet, a personal digital assistant, or a laptop. Further components may be feasible, in particular at least one of a data acquisition unit, a preprocessing unit, or a data storage unit. The processing device may, typically, be configured to perform at least one computer program, in particular at least one line of computer program code configured to execute at least one algorithm for determining data related to a progression of refractive values of a person, wherein the processing of the data may be performed in at least one of a consecutive or a parallel fashion.

According to the present disclosure, the processing device is configured to determine data related to a progression of refractive values of a person from data related to the person which may be received from the at least one input file. As generally used, the term "determining" or any grammatical variation thereof refers to a process of generating representative results which are, typically, denoted as "data." With particular regard to the present disclosure, the data generated in this fashion comprise pieces of information which are related to a forecast of refractive values of at least one eye of a person. Instead of the term "person," a different term, such as "user," "subject," "individual," or "wearer," may also be applicable.

As indicated above, the data related to the person comprise a refractive status of the person. Typically, the data related to the refractive status of the person may comprise at least one refractive value of the at least one eye of the person. As used herein, the term "at least one eye" refers to one eye or to both eyes of the person. As generally used, the term "refractive value" corresponds to at least one refractive error of at least one eye of a person, which can, in particular, be used for producing at least one optical lens, specifically at least one spectacle lens or at least one contact lens, each of which exhibits, based on the refractive values, a dioptric power which is capable of correcting the at least one refractive error of the at least one eye of the person. As further generally used, the term "progression of refractive values" refers to a forecast of a temporal alteration, in particular a decrease, especially a monotonous decrease, of the refractive values of the at least one eye of the person over a period of time. Based on standard ISO 13666:2019, referred herein as the "Standard," Section 3.5.2, the term "spectacle lens" refers to an optical lens which is used for correcting the at least one refractive error of the at least one eye of the person, wherein the optical lens is carried in front of the eye of the person, thereby avoiding a direct contact with the eye of the person. Consequently, the term "contact lens" refers to an optical lens which is used for correcting the at least one refractive error of the at least one eye of the person which is worn in direct contact with the eye of the person. Further, the term "glasses" refers to an element which comprises two individual spectacle lenses and a spectacle frame, wherein each spectacle lens is prepared for being received by the spectacle frame selected by the person.

With regard to the present disclosure, the at least one refractive value may, in particular, be selected from a value for a sphere, and, typically in addition, a value for a cylinder of the ocular lens in the at least one eye of the person. As defined in the Standard, Section 3.12.2, the term "spherical power," usually abbreviated to "sphere" or "sph," refers to a value of a back vertex power of a spherical-power lens. As defined in the Standard, Section 3.13.7, the term "cylinder," usually abbreviated to "cylinder" or "cyl," refers to an algebraic difference between principal powers with power of the principal meridian chosen for reference being subtracted from the other principal power.

Alternatively or in addition, the data related to the refractive status of the person may be or comprise at least one biometric value of the at least one eye of the person. As generally used, the term "biometric value" refers to a measured value which is related to at least one extension of at least one feature of the at least one eye in the person in three-dimensional space and may, thus, typically, be indicated by using a value and a corresponding unity, such as meter, which indicates a spatial extension. With regard to the present disclosure, the biometric values may, in particular, comprise both an axial length and a corneal radius of the at least one eye of the person, wherein an anterior chamber depth or an ocular lens thickness may, in addition, be used as at least one of the biometric values. However, selecting at least one different biometric value may also be feasible. Further, the person skilled in the art knows that the at least one refractive value of the at least one eye of the person is closely related to the at least one biometric value of the at least one eye of the person. In practice, known relationships exist that can be applied for converting first values related to at least one biometric value to second values related to at least one refractive value, or vice-versa. Consequently, both the at least one refractive value the person and the at least one biometric value of the at least one eye of the person are addressed by the term "refractive status" of the person.

As further generally used, the terms "refractive power" or simply "power" refer to, as defined in the Standard, Section 3.1.10, to a capacity of as lens, specifically of a spectacle lens or a contact lens, to alter at last one of a curvature or a direction of an incident wavefront by refraction. As further used herein, the term "myopia" relates to a refractive status of the person in which the refractive power of at least one eye of the person assumes a value below −0.5 dpt. As further generally used, the term "high myopia" refers to a refractive status of the person in which the refractive power of at least one eye of the person assumes a value below −6.0 dpt. As further generally used, the term "myopia progression" refers to a forecast of a temporal alteration, in particular a decrease, especially a monotonous decrease, of the refractive power of the at least one eye of the person over a period of time. Herein, the period of time for the forecast may cover a number of years, typically 1 year to 12 years, more typically 2 years to 10 years, in particular 4 years to 8 years. However using a different period of time may also be feasible. As further used herein, the term "myopia onset" refers to a point in time during the myopia progression at which the refractive power of the at least one eye of the person decreases from a value above −0.5 dpt to a value below −0.5 dpt.

As indicated above, the data related to a person, further, comprise personal data, namely age, gender and ethnicity of the person. As generally used, the term "age" refers to a time since a day of a birth of the person and may, typically, be indicated in years. The present disclosure may, particularly, be applicable to persons being children, juveniles, or young adults having an age of 4 years to 24 years, especially of 5 years to 20 years. However, the present disclosure can also be applied to persons having a different age. As further generally used, the term "gender" refers to an identity of the person with respect to the terms "female" and "male," while a non-binary identity may also be possible. As further generally used, the term "ethnicity" refers to an assignment of the person to a particular population. Not wishing to be bound by theory, although Morgan I. G., et al., see above, summarize that evidence and causal relationship between gender and ethnicity of the person, on one hand, and myopia progression on the other hand, are weak or inconsistent, still, a trained machine learning algorithm may, as expressed in WO 2020/083382 A1, generate more accurate predictions for a person belonging to at least one of a specific gender or a population compared to a machine learning algorithm trained by using a mixed population training set.

In accordance with the present disclosure, the data related to a person comprise at least one of a risk factor related to the person. As generally used, the term "risk factor" refers to a value of at least one of a condition or a process related to the person which has been demonstrated to increase or to decrease the myopia progression and/or to increase or decrease the point in time of myopia onset in the at least one eye of the person. Not wishing to be bound by theory, the risk factor may, according to Morgan I. G., et al., see above, to be useful for designing a myopia treatment, typically be selected to be carried by demonstration of a causal connection related to a defined mechanism between an assumed risk factor and an observed myopia treatment, especially by using associations with conditions or processes, on one hand, and myopia progression, on the other hand, that can be demonstrated using cross-sectional data or, typically, longitudinal data on defined populations. For definitions of different types of data, reference can be made to the description below.

In a particularly exemplary embodiment, the at least one risk factor may be selected from data related to the refractive status of at least one parent of the person. For the term "refractive status" reference can be made to the definition as provided above which is mutatis mutandis applicable to the at least one parent of the person. According to Morgan I. G., et al., see above, evidence and causal relationship between the refractive status of the at least one parent of the person, on one hand, and myopia progression on the other hand, is strong, irrespective of a discussion whether being based on passing on genetic variants or a myopiagenic lifestyle that predispose their children to myopia.

Alternatively or in addition, the at least one risk factor may be selected from data related to at least one parameter related to a behavior of the person. As generally used, the term "behavior" refers to a repeated activity of the person during which the at least one eye of the person is subject to an exposure of optical radiation. As further generally used, the term "optical radiation" refers to electromagnetic waves having a wavelength of 380 nm to 780 nm, defining the so-denoted "optical wavelength range," wherein radiation from adjacent wavelength ranges, especially from 100 nm to below 380 nm, denoted as "long ultra-violet wavelength range," and/or from above 780 nm to 1.5 μm, denoted as "near infrared wavelength range" can also be considered for the purposes of the present disclosure. Not wishing to be bound by theory, Morgan I. G., et al., see above, indicate that evidence and causal relationship between the behavior of the person, on one hand, and myopia progression on the other hand, is strong and causal, especially depending on at least one parameter of the optical radiation, in particular related to an intensity, a spectral distribution and a duration of the optical radiation, incident on the at least one eye of the person.

According to the present disclosure, the at least one parameter related to the behavior of the person is selected from data related to at least one of a first amount of time spent by the person on near vision working;

a second amount of time spent outdoors by the person.

As generally used, the term "near vision working" refers to a first type of repeated activity of the person dedicated to directing the eyes of the person to an object which is placed in a distance to the eyes of the person in a manner that the eyes of the person accommodate to a near point. As generally used, the term accommodating" or any grammatical variation thereof relates to adjusting the refraction of the eyes of the person to a retinal plane of the eyes of the person when imaging an object located in front of the eyes of the person between a near point and a far point. The term "far point" relates to an end point of a refractive direction of the eyes of the person without accommodation, while the term "near point" refers to a point indicating a smallest distance in front of the eyes of the person at which the object can still be sharply imaged on the retinal plane of the eyes of the person, the near point being an individual quantity particularly depending on the age of the person. Herein, a fixed location of the eyes of the person, especially on the cornea, e.g., a location of an observable corneal reflex, can serve as reference point for measuring the distance of the near point to the eyes of the person. In practice, the object of the near vision working of the person may, in particular, be a literary object or a mobile communication device. As used herein, the term "literary object" refers to a kind of object comprising printed information, especially selected from a book, a brochure or a newspaper. Further, the term "mobile communication device" refers to at least one electronic device which is configured to present information by using an electronically driven screen, which can be carried by the person and, can thus, move together with the person, especially selected from a smartphone, a notebook, a personal digital assistant, or a laptop. However, further kinds of objects may also be feasible.

As further generally used, the term "time spent outdoors" refers to a second type of repeated activity of the person which is performed by the person outside a building in open air, especially during or after pre-school or school, on weekends, or during vacations. As indicated above, the intensity of the optical radiation which is incident on the at least one eye of the person can be considerably increased during the second amount of time spent outdoors by the person. Not wishing to be bound by theory, Morgan I. G., et al., see above, indicate that associations between the time spent outdoors and a decrease of myopia progression are strong and consistently observed, while a controversy exists over whether increased time spent outdoors not only reduces the myopia progression but also an onset of myopia.

A further generally used, the term "amount of time" refers to a duration during which the respective repeated activity of the person is performed, especially by using average occupation of the person indicated in hours per day or hours per week. For a purpose of determining the amount of time, the period of time which is regularly spent outside vacations may be used; however it may be feasible to modify this value by adding the period of time, typically in addition, spent outside during the vacations, thereby taking into account the annual duration of the vacations compared to the annual duration of the school time or the pre-school time.

In a exemplary embodiment, the data related to a person may further comprise at least one type of myopia treatment to be applied to the person. As generally used, the term "type of myopia treatment" refers to at least one kind of preventive intervention which is configured to at least one of decreasing myopia progression or retarding myopia onset in the at least one eye of the person. In particular, the type of myopia treatment may comprise an application of at least one of an optical lens to the at least one eye of the person. Herein, the at least one of optical lens may, typically, be selected from or a spectacle lens or a contact lens. Especially on a type of myopia, the spectacle lens may, particularly, be selected from a bifocal lens, a progressive addition lens, a peripheral defocus lens, or a defocus incorporated multiple segments lens, while the contact lens may, typically, be selected from a multifocal contact lens or an orthokeratologic lens. As defined in the Standard, Section 3.7.3, the term "bifocal lens" refers to a particular type of spectacle lens having two portions, wherein each portion has a different value for the refractive power. Similarly, the term "progressive addition lens" refers to, as defined in the Standard, Section 3.7.7-8, to another type of spectacle lens having a smooth variation of refractive power without discontinuity over a surface of lens. Further, the term "peripheral defocus lens" refers to a further type of spectacle lens having a change of optical power from a central optical zone to a periphery of the lens, whereby a peripheral defocus is induced at eccentric regions of the retina. Further, the term "defocus incorporated multiple segments lens" refers to a further type of spectacle lens which comprises a central optical zone for correcting distance refractive errors, and an annular multiple focal zone which may comprise segments having a different refractive power compared to the central optical zone. Further, the term "orthokeratologic lens" refers to a gas-permeable contact lens configured to temporarily reshape the cornea to alter the refractive power of the at least one eye of the person. However, using other types of spectacle lenses or contact lenses may also be feasible.

Alternatively or in addition, the type of myopia treatment may be selected from an application of at least one of a dose of a drug, specifically of atropine, or of refractive surgery. However, applying at least one of a drug or refractive surgery may only correct a current refractive error but may not be sufficient to reduce the further myopia progression.

Further according to the present disclosure, the processing device is, further, configured to determine the data related to the progression of refractive values of the person by using at least one machine learning algorithm. As generally used, the term "machine learning" refers to a process of applying artificial intelligence to automatically generate a model for at least one of classification or regression. Herein, at least one machine learning algorithm configured to generate the desired model based on a large number of training data sets can, typically, be used. As further generally used, the term "training" indicates that a performance of the method step of determining the desired data is improved during a training phase by providing a plurality of training data sets and executing them by the particular method step. Herein each training data set which is used for a training purpose resembles an expected data set, such as the data related to the progression of refractive values of the person, which, however, comprises known data. The particular method step is, then, performed with the particular training data set, wherein the result for the content as obtained in this fashion is adjusted to the known data from the particular training data set. Herein, a plurality of training data sets is iteratively applied during the training phase in order to improve an approximation of the result as achieved during the execution of the particular method step, specifically by repeated the training of the particular method step until a deviation between the data as obtained by executing the particular method step and the known data as comprised by each training data set may be below a threshold. After the training phase, the data as obtained by executing the particular method step can reasonably be expected to approximate the known data in the same manner as achieved during the training phase. In this fashion, a more accurate determination of the data can be obtained during the training phase. Thus, after the training phase, the desired performance of the particular method step may be acquired.

The machine learning algorithm used herein for determining the desired data related to the progression of refractive values of the person comprises at least one prediction model for determining a relationship between the data related to the person and the progression of the refractive values of the person. Typically, the one or more models may be selected from a linear prediction model, specifically from at least one of Support Vector Regression (SVR) or Gaussian Process Regression (GPR). However, using one or more further types of models may also be feasible.

In a particularly exemplary embodiment, the at least one machine learning algorithm may comprise applying a first prediction model which uses longitudinal data and a second prediction model which uses cross-sectional data. As generally used herein, the terms "first" or "second" are considered as a description of an element without specifying an order or a chronological sequence and without excluding a possibility that other elements of the same may be present. As further generally used, the term "longitudinal data" refers to a plurality of first pieces of data which are related to a particular person, wherein the term "cross-sectional data" comprise at least one second piece of data related to a plurality of different persons. By way of example, the longitudinal data refers to a plurality of refractive values, specifically values for a sphere, which are related to the same person over a period of time, thereby providing a progression of the refractive values over an increasing age of the particular person. In contrast hereto, the cross-sectional data are related to the same refractive values, specifically value for a sphere, for a plurality of different persons having the same age and, typically, at least one of the same gender and of the same ethnicity.

In a this particularly exemplary embodiment, the first prediction model using longitudinal data may, typically, be a first linear prediction model using Support Vector Regression (SVR) while the second prediction model using cross-sectional data may be a second linear prediction model using Gaussian Process Regression (GPR). As generally used, the terms "Support Vector Regression" or "SVR" refer to a machine learning tool for classification and regression, accounting as a nonparametric technique that relies on kernel functions. As further generally used, the terms "Gaussian Process Regression" or "GPR" refer to a machine learning tool which uses nonparametric kernel-based probabilistic models for prediction.

In a particular embodiment, a total data input into the at least one machine learning algorithm may comprise a first amount of longitudinal data input and a second amount of cross-sectional data input, wherein both the first amount of data and the second amount of data are used for determining the desired data related to the progression of refractive values of the person. Preferentially, the total data input may be distributed in a fashion that the first amount may be of 30% to 70%, typically of 50% to 70%, while the second amount may be of 30% to 70%, typically of 30% to 50%, wherein the first amount and the second amount add up to 100%. However, using a different kind of distribution may also be feasible.

In a further particular embodiment, the machine learning algorithm may comprise using at least two different prediction models that may be combined. Herein, the first prediction model may generate intermediate prediction data, specifically a relationship between the data related to the person and a ratio of the axial length divided by the corneal radius data, wherein the intermediate prediction data, specifically the ratio of the axial length divided by corneal radius data, may, typically, be used as input into the second prediction model, especially for a prediction of the refractive power. However, using a further type of intermediate prediction data may be also feasible.

In a further particular embodiment, the processing device may, further, be configured to determine at least one further piece of data as the data related to the progression of the refractive values of the person. Herein, the at least one further piece of data may, typically, be selected from at least one of

- a ranking of the person compared to a plurality of further persons;
- a risk of myopia for the person;
- a risk of high myopia for the person.

As generally used, the term "ranking" or any grammatical variation thereof refers to comparing results of a particular person with results of a plurality of further persons for whom the same kind of data have been determined. In particular, the result as achieved by the ranking can be indicated by a number or, preferentially, by a percentage which indicates a position of the particular person with respect to the further persons, specifically of the same age and, typically, at least one of the same gender and of the same ethnicity.

As further used herein, the term "risk of myopia" refers to a first probability that the person develops myopia by acquiring the value for myopia onset during the course of the progression of the refractive values. In particular, the risk of myopia can be indicated by a qualifier selected from a list, wherein each item in the list refers to a particular myopia status. Specifically, the qualifier can be selected from "high" and "low," wherein the term "high" may indicate that, according to the prediction, the refractive power of at least one eye of the person assumes a value below −0.5 dpt along the course of the progression of the refractive values, whereas the term "low" may indicate that, according to the prediction, the refractive power of the at least one eye of the person stays at or above the of −0.5 dpt along the course of the progression of the refractive values.

Similarly, the term "risk of high myopia" refers to a further probability that the person develops high myopia by acquiring a refractive value defined as a high myopia value during the course of the progression of the refractive values. In particular, the risk of high myopia can be indicated by a further qualifier selected from a further list, wherein each item in the further list refers to a particular high myopia status. Specifically, the qualifier can be selected from "high" and "low," wherein the term "high" may indicate that, according to the prediction, the refractive power of at least one eye of the person assumes a value below −6.0 dpt along the course of the progression of the refractive values, whereas the term "low" may indicate that, according to the prediction, the refractive power of the at least one eye of the person stays at or above the of −6.0 dpt along the course of the progression of the refractive values.

In a further aspect, the present disclosure relates to a system for providing data related to a progression of refractive values. As generally used, the term “system” refers to a combination of at least two components each of which is configured to perform a particular task, wherein, however, the at least two components may cooperate and/or interact with each other in order to achieve the desired task.

According to the present disclosure, the system comprises:

- at least one input interface configured to receive data related to the person as described elsewhere herein;
- a processing device as described elsewhere herein; and
- at least one output interface configured to provide data related to the progression of the refractive values of the person.

With respect to the processing device, reference can be made to the description thereof throughout this document.

Further, the processing device may, typically, comprise at least one communication interface configured to provide communication with both the at least one input interface and the at least one output interface. As generally used, the term “communication interface” refers a transmission channel being designated for a transmission of data. Typically, the communication interface may be arranged as a unidirectional interface which is configured to forward at least one piece of data into a single direction, from the at least one input interface to the processing device, or from the processing device to the at least one output interface. Alternatively, the communication interface may be arranged as a bidirectional interface which is configured to forward at least one piece of data into one of two directions, from a communication unit, which may comprise both the input interface and the output interface, to the processing device, or vice versa. For a purpose of data transmission, the communication interface may comprise at least one of wire-bound element or a wireless element, wherein the wireless element may be configured to operate by using at least one wireless communication protocol, such as Wi-Fi or Bluetooth. In a particularly exemplary embodiment, the communication may be or comprise an encrypted data transfer or an encrypted data exchange. However, a further kind of communication interface may also be feasible.

As generally used, the term “input interface” refers to an apparatus which is configured to receive at least one piece of data, specifically the data related to the person as described above or below in more detail. For this purpose, the data can, typically, be provided in form of at least one of an input file or as input data by using a graphical user interface (GUI), and forwarded to the processing device for determining the desired data related to the progression of the refractive values of the person. As generally used, the terms “graphical user interface” or “GUI” refer to a type of input interface which is configure to receive the desired personal data from a graphical interaction with a user. Herein, the user may be selected from at least one of an eye care professional, specifically an optician, optometrist or ophthalmologist, or; or the person subject to myopia or a related person, especially a parent of the person or a nurse caring for the person. The graphical interaction may comprise presenting graphical icons on a screen to the user, recording a reaction of the user, and determining the desired input data by evaluating the reaction of the user. For this purpose, at least one touchscreen configured to provide access to inputting at least one piece of data, specifically the data related to the person, may be used. However, other devices may also be feasible, such as at least one of a camera or a scanner configured to generate an input file to be processed by the processing device for acquiring the desired input data.

As further generally used, the term “output interface” refers to a further apparatus which is configured to provide at least one output file comprising at least one further piece of data, specifically the desired data related to the progression of the refractive values of the person. Herein, the processing device may, typically, be configured to provide the data related to the progression of the refractive values of the person via the by using, typically, the same or a different graphical user interface which displays the data comprised by the output file to the user, in particular by using a graphical user interface, typically the same graphical user interface as used for the input interface. As indicated above, the user may be selected from at least one of an eye care professional, such as an optician, an optometrist or an ophthalmologist; or the person subject to myopia or a related person, especially a parent of the person or a nurse caring for the person. Alternatively or in addition, the processing device may, typically, be configured to provide the data related to the progression of the refractive values of the person in form of a structured output file to the at least one output interface. As generally used, the term “structured output file” refers to a file in which the pieces of data follow a predefined arrangement, in particular, in order to facilitate further processing of the output file by a recipient, specifically by at least data processing system in an office or practice of the eye care professional or in a hospital. Further, at least one additional output interface may be feasible, specifically at least one further kind of output interface configured to provide the received at least one further piece of data, specifically the data related to the progression of the refractive values of the person as determined by the processing device, to a further recipient, especially at least one data storage unit, which may be configured to store a copy of the output data, a printer configured to print the output data, or a microphone configured to read the output data, possibly each in a different format. However, a further kind of output interface may also be feasible.

In a particularly exemplary embodiment, the system may comprise or may be implemented by using at least one mobile communication device. As generally used, the term “mobile communication device” refers to at least one of a smartphone, a tablet, a personal digital assistant, or a laptop, which can be carried by the person and, can thus, move together with the person. However, further kinds of mobile communication devices may also be conceivable. In general, the at least one mobile communication device may comprise the at least one input interface, the at least one processing device, and the at least one output interface. A mobile operating system running on the at least one mobile communication device may be configured to facilitate a use of software, such as the graphical user interface; multimedia functionalities; and communication facilities, such as internet or at least one wireless communications protocol, such as Wi-Fi or Bluetooth. Herein, the mobile communication device may, particularly, be useful for collecting the desired input data from a user, specifically by applying a graphical user interface to be used for self-inputting input data known by the user.

As generally used, the term “providing” or any grammatical variation thereof refers to forwarding a prediction with respect to the data related to the progression of the refractive values of the person to at least one output interface, such as the at least one output interface as described above and below in more detail. As used herein, the term “prediction” refers to a prognosis of the of the data related to the progression of the refractive values of the person over a future period of time, which may cover a number of years, typically 1 year to 12 years, more typically 2 years to 10 years, in particular 4 years to 8 years. However using a different period of time may also be feasible.

In addition, the at least one output interface may, further, be configured to further at least one percentile referencing for the refractive values and/or a modified progression of refractive values of the person taking in to account the at least one type of myopia treatment. As generally used, the term "percentile referencing" refers to providing a value based on population-based data covering a range of ages. Typically a $97^{th}$ percentile, a $50^{th}$ percentile and a $3^{rd}$ percentile for a plurality of persons having the same age may be provided; herein, the $97^{th}$ percentile, the $50^{th}$ percentile and the $3^{rd}$ percentile indicate that the related curve covers 97%, 50%, or 3% of the population on which the percentile is based, respectively. However, using, alternatively or in addition, at least one other percentile may also be feasible, such as at least one of a $1^{st}$ percentile, a $2^{nd}$ percentile, a $5^{th}$ percentile; a 95th percentile, a $98^{th}$ percentile, or a $99^{th}$ percentile.

As further used herein, the term "modified progression" refers to an altered course of the refractive values of the person in which the implementation of the at least one type of myopia treatment as described above in more detail has been taken into account. For an example, reference can be made to the FIGS. as presented below.

In a further aspect, the present disclosure relates to a computer-implemented method for determining data related to a progression of refractive values of a person. Herein, the method comprises the steps of

- receiving data related to a person, comprising
  - a refractive status of the person;
  - age, gender and ethnicity of the person; and
  - at least one risk factor related to the person;
- determining data related to a progression of refractive values of the person using at least one machine learning algorithm, wherein the at least one machine learning algorithm comprises at least one prediction model for determining a relationship between the data related to the person and the progression of the refractive values of the person.

In a further aspect, the present disclosure relates to a computer-implemented method for providing data related to a progression of refractive values of a person, wherein the method comprises the following steps:

- receiving data related to the person according to the method for determining data related to a progression of refractive values of a person by using at least one input interface;
- determining data related to a progression of refractive values of a person according to the method for determining data related to a progression of refractive values of a person by using at least one processing device as described above or below;
- providing the data related to the progression of the refractive values of the person by using at least one output interface.

Various embodiments can be conceived for implementing the methods according to the present disclosure. According to a first embodiment, all method steps can be performed by using a single processing device, such as a computer, especially a stand-alone computer, or an electronic communication unit, specifically a smartphone, a tablet, a personal digital assistant, or a laptop. In this embodiment, the single processing device may be configured to exclusively perform at least one computer program, in particular at least one line of computer program code configured to execute at least one algorithm, as used in at least one of the methods according to the present disclosure. Herein, the computer program as executed on the single processing device may comprise all instructions causing the computer to carry out the at least one of the methods according to the present disclosure. Alternatively or in addition, at least one method step can be performed by using at least one remote processing device, especially selected from at least one of a server or a cloud computer, which is not located at the site of the user when executing the at least one method step. In this further embodiment, the computer program may comprise at least one remote portion to be executed by the at least one remote processing device to carry out the at least one method step. Further, the computer program may comprise at least one interface configured to forward and/or receive data to and/or from the at least one remote portion of the computer program.

The above-described methods according to the present disclosure are computer-implemented methods. As generally used, the term "computer-implemented method" refers to a method involving at least one programmable device, particularly from a mobile communication device. However, a further kind of programmable device may also be feasible. Herein, the at least one programmable device may, in particular, comprise or have access to the processing device, wherein at least one of the features of the methods is performed by using at least one computer program. In accordance with the present disclosure, the computer program may be provided on the at least one programmable device, or the at least one mobile communication device may have access to the computer program via a network, such as an in-house network or the internet.

In a further aspect, the present disclosure relates to a computer program comprising instructions which, when the program is executed by a computer, cause the computer to carry out the methods according to any one of the preceding method embodiments. Specifically, the computer program may be stored on a computer-readable, non-transitory data carrier. Thus, specifically, any one of the method steps as indicated above may be performed by using a computer or a computer network, typically by using a computer program.

In a further aspect, the present disclosure relates to a computer program product having program code means, in order to perform the methods according to the present disclosure when the program is executed on a computer or computer network. Specifically, the program code means may be stored on a computer-readable data carrier.

In a further aspect, the present disclosure relates to a data carrier having a data structure stored thereon, which, after loading into a computer or computer network, such as into a working memory or main memory of the computer or computer network, may execute any one of the methods according to one or more of the embodiments disclosed herein.

In a further aspect, the present disclosure relates to a computer program product with program code means stored on a machine-readable carrier, in order to perform the methods according to one or more of the embodiments disclosed herein, when the program is executed on a computer or computer network. As used herein, the term "computer program product" refers to the program as a tradable product. The product may generally exist in an arbitrary format, such as in a paper format, or on a computer-readable data carrier. Specifically, the computer program product may be distributed over a data network, such as the internet.

In a further aspect, the present disclosure relates to a modulated data signal which comprises instructions read-able by a computer system or computer network, for performing any one of the methods according to one or more of the embodiments as disclosed herein.

In a further aspect, the present disclosure relates to a method for producing at least one spectacle lens. Accordingly, the producing of the at least one spectacle lens comprises processing at least one lens blank by using at least one manufacturing device which employs data related to refractive values as determined by the method for determining data related to a progression of refractive values of a person, in particular, by using the processing device, wherein the data are forwarded to the at least one manufacturing device by using the method for providing data related to a progression of refractive values of a person as described elsewhere herein.

For further details with respect to the methods and the computer program as described herein, reference can be made to the description throughout this document.

With respect to the prior art, the device, the system, the computer-implemented methods and computer programs according to the present disclosure exhibit advantages. In particular, they are capable of improving the prediction of both myopia onset and myopia progression. Herein, the input data which may, typically, be selected for the algorithm are typical input data which can, normally, be accessed by an eye care professional, specifically by an optician, optometrist or ophthalmologist; or by the person subject to myopia or a related person, especially a parent of the person or a nurse caring for the person. As a result, the present disclosure provides for a flexible application of the algorithm and can support the eye care professional or the end consumer with an accurate prediction with respect to the progression of the refractive errors in one or both eyes of the person. Herein, the prediction can allow stablishing prevention strategies for both myopia progress and myopia onset.

As used herein, the terms "have," "comprise," or "include" or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B," and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

As further used herein, the terms "typically," "more typically," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an exemplary embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

Summarizing, the following exemplary embodiments according to the following Clauses are particularly typical within the scope of the present disclosure:

Clause 1: A processing device for determining data related to a progression of refractive values of a person, wherein the processing device is configured to receive data related to a person, comprising a refractive status of the person;

age, gender and ethnicity of the person; and at least one risk factor related to the person;

determine data related to a progression of refractive values of the person using at least one machine learning algorithm, wherein the at least one machine learning algorithm comprises at least one prediction model for determining a relationship between the data related to the person and the progression of the refractive values of the person.

Clause 2: The processing device according to the preceding clause, wherein the at least one risk factor is a value referring to at least one of a condition or a process related to the person having been demonstrated to increase or to decrease at least one of a myopia progression or a point in time of myopia onset in the at least one eye of the person.

Clause 3: The processing device according to any one of the preceding clauses, wherein the at least one risk factor is selected from data related to at least one of:

the refractive status of at least one parent of the person; or at least one parameter related to a behavior of the person.

Clause 4: The processing device according to the preceding clause, wherein the at least one parameter related to the behavior of the person is selected from data related to at least one of:

a first amount of time spent by the person on near vision working; or a second amount of time spent outdoors by the person.

Clause 5: The processing device according to the preceding clause, wherein the first amount of time is a first duration during which the person repeatedly performs near vision working.

Clause 6: The processing device according to any one of the two preceding clauses, wherein the near vision working refers to a first type of repeated activity of the person dedicated to directing the eyes of the person to an object being placed in a distance to the eyes of the person in a manner that the eyes of the person accommodate to a near point.

Clause 7: The processing device according to any one of the three preceding clauses, wherein the second amount of time is a second duration during which the person spends time outdoors.

Clause 8: The processing device according to any one of the four preceding clauses, wherein the time spent outdoors is a second type of repeated activity of the person which is performed by the person outside a building in open air, especially during or after pre-school or school, on weekends, or during vacations.

Clause 9: The processing device according to the preceding clause, wherein the second type of repeated activity of the person is performed by the person after pre-school or school, on weekends, or during vacations.

Clause 10: The processing device according to any one of the six preceding clauses, wherein at least one of the first amount of time or the second amount of time is indicated by using an average occupation of the person indicated in hours per day or in hours per week.

Clause 11: The processing device according to any one of the preceding clauses, wherein the refractive status is selected from at least one of:

at least one refractive value of at least one eye; or at least one biometric value of the at least one eye.

Clause 12: The processing device according to the preceding clause, wherein the at least one refractive value of at least one eye is selected from a value for a sphere of the ocular lens in the at least one eye.

Clause 13: The processing device according to the preceding clause, wherein the at least one refractive value of at least one eye is, in addition, selected from a value for a cylinder of the ocular lens in the at least one eye.

Clause 14: The processing device according to any one of the three preceding clauses, wherein the at least one biometric value of the at least one eye is a measured value related to at least one extension of at least one feature in the at least one eye in three-dimensional space.

Clause 15: The processing device according to the preceding clause, wherein the at least one biometric value of the at least one eye comprises an axial length and a corneal radius of the at least one eye.

Clause 16: The processing device according to the preceding clause, wherein the at least one biometric value of the at least one eye of the person further comprises at least one of an anterior chamber depth or an ocular lens thickness of the at least one eye.

Clause 17: The processing device according to any one of the preceding clauses, wherein the data related to the person further comprises at least one type of myopia treatment.

Clause 18: The processing device according to the preceding clause, wherein the at least one type of myopia treatment is selected from an application of at least one of:

an optical lens selected from a contact lens or a spectacle lens;

a dose of a drug; or refractive surgery.

Clause 19: The processing device according to the preceding clause, wherein the contact lens is selected from a multifocal contact lens.

Clause 20: The processing device according to any one of the two preceding clauses, wherein the spectacle lens is selected from a bifocal lens, a progressive addition lens, a peripheral defocus lens, or a defocus incorporated multiple segments lens.

Clause 21: The processing device according to any one of the preceding clauses, wherein the at least one machine learning algorithm comprises using a first prediction model and a second prediction model, wherein the first prediction model generates intermediate prediction data, and wherein the intermediate prediction data are used as input for the second prediction model.

Clause 22: The processing device according to the preceding clause, wherein the first prediction model generates a relationship between the data related to the person and the progression of the refractive values of the person.

Clause 23: The processing device according to the preceding clause, wherein the first prediction model generates a ratio of an axial length divided by a corneal radius for the person.

Clause 24: The processing device according to any one of the two preceding clauses, wherein the relationship as generated by the first prediction model is used as input into the second prediction model.

Clause 25: The processing device according to the preceding clause, wherein the ratio of the axial length divided by the corneal radius data is used as the input into the second prediction model.

Clause 26: The processing device according to any one of the five preceding clauses, wherein the first prediction model uses longitudinal data, wherein the longitudinal data comprise a plurality of first pieces of data related to a particular person; and, wherein the second prediction model uses cross-sectional data, wherein the cross-sectional data comprise at least one second piece of data related to a plurality of different persons.

Clause 27: The processing device according to the preceding clause, wherein the longitudinal data refers to a plurality of refractive values related to the same person over a period of time.

Clause 28: The processing device according to the preceding clause, wherein the longitudinal data provide a progression of the refractive values over an increasing age of the same person.

Clause 29: The processing device according to any one of the three preceding clauses, wherein the cross-sectional data are related to the same refractive values for a plurality of different persons having the same age.

Clause 30: The processing device according to any one of the four preceding clauses, wherein the first prediction model is a first linear prediction model using Support Vector Regression (SVR).

Clause 31: The processing device according to any one of the five preceding clauses, wherein the second prediction model is a second linear prediction model using Gaussian Process Regression (GPR).

Clause 32: The processing device according to any one of the six preceding clauses, wherein a total data input into the at least one machine learning algorithm comprises a first amount of longitudinal data input and a second amount of cross-sectional data input.

Clause 33: The processing device according to the preceding clause, wherein the first amount is of 30% to 70%.

Clause 34: The processing device according to any one of the two preceding clauses, wherein the second amount is of 30% to 70%.

Clause 35: The processing device according to any one of the three preceding clauses, wherein the first amount and the second amount add up to 100%.

Clause 36: The processing device according to any one of the preceding clauses, wherein the processing device is further configured to determine at least one of a ranking of the person compared to a plurality of further persons;

a risk of myopia for the person;

a risk of high myopia for the person.

Clause 37: The processing device according to the preceding clause, wherein the ranking refers to comparing results of the person with results of a plurality of further persons for whom the same kind of data have been determined.

Clause 38: The processing device according to any one of the two preceding clauses, wherein the risk of myopia refers to a probability that the person develops myopia by acquiring a value for myopia onset during a course of the progression of the refractive values.

Clause 39: The processing device according to the preceding clause, wherein myopia relates to a refractive status of the person in which the refractive power of at least one eye of the person assumes a value below −0.5 dpt.

Clause 40: The processing device according to any one of the two preceding clauses, wherein the value for myopia onset is a point in time during myopia progression at which the refractive power of the at least one eye of the person decreases from a value above −0.5 dpt to a value below −0.5 dpt.

Clause 41: The processing device according to any one of the five preceding clauses, wherein the risk of high myopia refers to a further probability that the person develops high myopia by acquiring a refractive value defined as a high myopia value during the course of the progression of the refractive values.

Clause 42: The processing device according to the preceding clause, wherein high myopia refers to a refractive status of the person in which the refractive power of at least one eye of the person assumes a value below −6.0 dpt.

Clause 43: A system for providing data related to a progression of refractive values of a person, the system comprising

- at least one input interface configured to receive data related to the person according to one of the preceding clauses;
- a processing device according to one of the preceding clauses; and
- at least one output interface configured to provide data related to the progression of the refractive values of the person.

Clause 44: The system according to the preceding clause, wherein the at least one output interface is further configured to further provide at least one of

- at least one percentile referencing for the refractive values;
- a modified progression of refractive values of the person considering an implementation of the at least one type of myopia treatment.

Clause 45: The system according to the preceding clause, comprising a graphical user interface which is designated as at least one of the input interface and the output interface.

Clause 46: The system according to any one of the preceding system clauses, wherein the at least one percentile referencing is provided for population-based data covering a range of ages.

Clause 47: The system according to any one of the preceding system clauses, wherein the at least one percentile referencing comprises at least one of a

- $1^{st}$ percentile, a $2^{nd}$ percentile, a $3^{rd}$ percentile, or a $5^{th}$ percentile;
- a $50^{th}$ percentile; and
- at least one of a $95^{th}$ percentile, a $97^{th}$ percentile, a $98^{th}$ percentile, or $99^{th}$ percentile.

Clause 48: The system according to any one of the preceding system clauses, wherein the modified progression refers to an altered course of the refractive values of the person considering the implementation of the at least one type of myopia treatment.

Clause 49: A computer-implemented method for determining data related to a progression of refractive values of a person, wherein the method comprises the steps of:

- receiving data related to a person, comprising
  - a refractive status of the person;
  - age, gender and ethnicity of the person; and
  - at least one risk factor related to the person;
- determining data related to a progression of refractive values of the person using at least one machine learning algorithm, wherein the at least one machine learning algorithm comprises at least one prediction model for determining a relationship between the data related to the person and the progression of the refractive values of the person.

Clause 50: The method according to the preceding clause, wherein the at least one machine learning algorithm comprises using a first prediction model and a second prediction model, wherein the first prediction model generates intermediate prediction data, and wherein the intermediate prediction data are used as input for the second prediction model.

Clause 51: The method according to the preceding clause,

- wherein the first prediction model uses longitudinal data, wherein the longitudinal data comprise a plurality of first pieces of data related to a particular person; and,
- wherein the second prediction model uses cross-sectional data, wherein the cross-sectional data comprise at least one second piece of data related to a plurality of different persons.

Clause 52: A computer-implemented method for providing data related to a progression of refractive values of a person, the method comprising the following steps:

- receiving data related to the person according to one of the preceding method claims by using at least one input interface;
- determining data related to a progression of refractive values of a person according to any one of the preceding methods claims by using at least one processing device; and
- providing the data related to the progression of the refractive values of the person by using at least one output interface.

Clause 53: A computer program comprising instructions which, when the program is executed by a computer, cause the computer to carry out the method according to any one of the preceding method clauses.

Clause 54: A method for producing at least one spectacle lens, wherein the producing of the at least one spectacle lens comprises processing at least one lens blank by using data related to refractive values as determined by a method for determining data related to a progression of refractive values of a person according to any one of the preceding clauses referring to the method for determining data related to a progression of refractive values of a person.

BRIEF DESCRIPTION OF THE DRAWINGS

Further optional features and embodiments of the present disclosure are disclosed in more detail in the subsequent description of exemplary embodiments. Therein, the respective optional features may be implemented in an isolated fashion as well as in any arbitrary feasible combination, as the skilled person will recognize. It is emphasized here that the scope of the disclosure is, however, not restricted to the exemplary embodiments. In the drawings.

DESCRIPTION OF EXEMPLARY EMBODIMENTS

Figure 1:
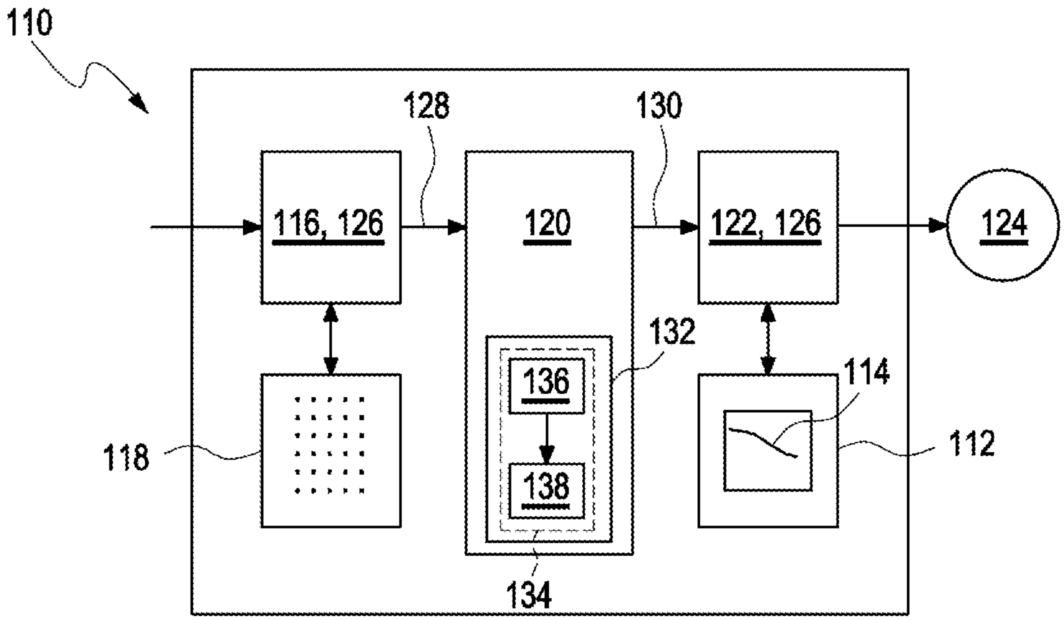
FIG. 1 illustrates an exemplary embodiment of a system for providing data related to a progression of refractive values according to the present disclosure.

FIG. 1 illustrates an exemplary embodiment of a system 110 for providing output data 112 comprising a prediction with respect to a progression 114 of refractive values of a person according to the present disclosure. Herein, the person may be a child, a juvenile or a young adult having an age of 4 years to 24 years, especially of 5 years to 20 years; however applying the present disclosure to a person having a different age may also be feasible. The prediction may cover a period of time, especially a number of years, typically 1 year to 12 years, more typical 2 years to 10 years, in particular 4 years to 8 years; however using a different period of time may also be feasible.

The prediction may, in particular, be used as a forecast for myopia progression and/or myopia onset in one or both eyes of the person. Herein, the myopia progression indicates a decrease, especially a monotonous decrease, of the refractive power of one or both eyes of the person over the period of time as indicated above. Further, myopia describes a refractive status of one or both eyes of the person having a refractive power below −0.5 dpt, whereas high myopia describes a refractive status of one or both eyes of the person having a refractive power below −6.0 dpt. Further, the myopia onset refers to a point in time during the myopia progression at which the refractive power of one or both eyes of the person decreases from a value above −0.5 dpt to a value below −0.5 dpt.

As schematically depicted in FIG. 1, the system 110 comprises at least an input interface 116 configured to receive input data 118 related to the person, a processing device 120 configured to determine the output data 112 related to the progression 114 of the refractive values of the person, and an output interface 122 configured to provide the output data 112 related to the progression 114 of the refractive values of the person to one or more recipients 124. The one or more recipients 124 may be an eye care professional, such as an optician, an optometrist or an ophthalmologist; or an end consumer, such as the person subject to myopia or a related person, especially a parent of the person or a nurse caring for the person.

The input interface 116 is configured to receive the input data 118, typically in form of an input file. In particular for obtaining the input data 118, the input interface 116 may, typically, be implemented as a graphical user interface 126 which may be configured to retrieve the desired input data 118, such as by allowing the one or more recipients 124 to enter the desired input data 118, such as by using a keyboard, a touchscreen and/or a microphone; however further possibilities are conceivable. An exemplary embodiment of the graphical user interface 126 is illustrated below in FIG. 3.

Further, the processing device 120 can, typically, be configured to provide the output data 112 in form of a structured output file to the output interface 122. For this purpose, the output data 112 can be provided to the one or more recipients 124 by using a screen, a printer and/or a loudspeaker. Typically, the output interface 122 can be implemented by using the same graphical user interface 126 which may, further, be configured to provide the desired output data 112 to the one or more recipients 124. However, using a different graphical user interface may also be feasible.

A first communication interface 128 can be configured to provide communication between the input interface 116 and the processing device 120, while a second communication interface 130 can be configured to provide communication between the processing device 120 and the output interface 122. As schematically illustrated in FIG. 1, each communication interface 128, 130 may be implemented as a unidirectional interface which may be configured to forward the respective pieces of data into the indicated single direction in a wire-bound element and/or a wireless fashion, typically via encrypted data transfer. However, a further kind of communication interface may also be feasible.

In accordance with the present disclosure, the processing device 120 is configured to receive the input data 118 related to the person, wherein the input data 118 comprise

- a refractive status of the person;
- age, gender and ethnicity of the person; and
- one or more risk factors related to the person.

In addition, the input data 118 may comprise one or more data items, typically one or more types of myopia treatments to be applied to the person.

Further, the processing device 120 is configured to determine the output data 112 related to the progression 114 of the refractive values of the person by a more machine learning algorithms 132, which comprises one or more prediction models 134 for determining a relationship between the input data 118 related to the person and the output data 112 related to the progression 114 of the refractive values of the person. As described above and below in more detail, using the one or more risk factors related to the person and/or the one or more types of myopia treatment to be applied to the person in addition to the refractive status, the age, the gender and the ethnicity of the person as the input data 118, considerably improves determining the progression 114 of the refractive values of the person as determined by using the processing device 120.

As further schematically depicted in FIG. 1, the machine learning algorithm 132 may, typically use a first prediction model 136 which uses longitudinal data as the input data 118 and a second prediction model 138 which uses cross-sectional data as the input data 118. For further details with respect to the different types of prediction models 136, 138 and the different kinds of data, reference can be made to the description below.

Figure 2:
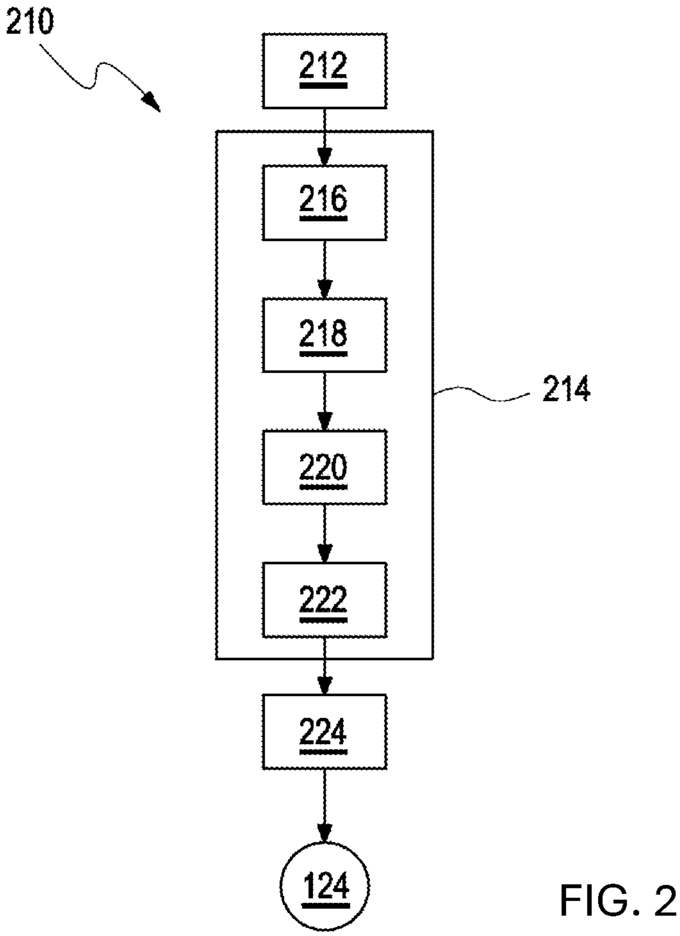
FIG. 2 illustrates an exemplary embodiment of a computer-implemented method for providing the data related to the progression of the refractive values of the person according to the present disclosure.

FIG. 2 illustrates an exemplary embodiment of a computer-implemented method 210 for providing the output data 112 related to the progression 114 of the refractive values of the person according to the present disclosure.

In a receiving step 212, the input data 118 related to the person are received by the input interface 116, such as by the recipient who uses the graphical user interface 126; however further possibilities are conceivable. Herein, the input data 118 may, typically, be compiled in form of an input matrix x and forwarded to the processing device 120. By way of example, the input matrix x may comprise the following entries:

- a value indicating a current refractive status of the person, typically a spherical value for both eyes of the person;
- a value indicating an age of the person;
- a number indicating a gender of the person;
- a number indicating an ethnicity of the person;
- a value indicating a current refractive status of both parents of the person, typically a spherical value for both eyes of both parents of the person;
- a value indicating a first amount of time spent by the person on near vision working;
- a value indicating a second amount of time spent outdoors by the person; and
- a number indicating a type of optical lens selected from a particular contact lens or a particular spectacle lens as the type of myopia treatment to be applied to the person.

Alternatively or in addition, the input matrix x may comprise other or further entries, however, only as long as a minimum number of entries according to the present disclosure is comprised hereby.

In a determining step 214, the output data 112 related to the progression 114 of the refractive values of the person are determined from the input data 118. Herein, the input data 118, typically compiled in form of the input matrix x, and forwarded to the processing device 120, in particular via the first communication interface 128, is used. For this purpose, the machine learning algorithm 132 comprising the one or more prediction models 134 for determining the relationship between the input data 118 related to the person and the output data 112 related to the progression 114 of the refractive values of the person is used. As indicated above, the machine learning algorithm 132 may, typically, use the first prediction model 136 which employs longitudinal data as the input data 118 and the second prediction model 138 which employs cross-sectional data as the input data 118.

In a particularly exemplary embodiment, the determining step 214 can comprise a first prediction step 216, in which the machine learning algorithm 132 may use the first prediction model 136 to predict a ratio R of the axial length divided by the corneal radius data, specifically by using Support Vector Regression (SVR). For this purpose, Equation (1)

$$R = \sum_{n=1}^{N} (\alpha_n - \alpha_n^*) G(x_n, x) + b \quad \text{(Eq. 1)}$$

may be used, wherein

R is the ratio of the axial length divided by the corneal radius data as predicted for a given input matrix x as described above;

N is a total number of trained support vectors, wherein each support vector comprises a matrix $x_n$ and Lagrange multipliers of this vector $\alpha_n$ and $\alpha_n$*;

G(xn, x) is a kernel function adopted for the first prediction model 136, wherein the kernel function could be selected from a linear function or a nonlinear function; and b is a bias value, which is determined and stored during the support vector training process.

Further in this particularly exemplary embodiment, the determining step 214 can comprise a second prediction step 218, in which the machine learning algorithm 132 may use the second prediction model 138 to predict the progression 114 of the refractive values of the person, specifically by using Gaussian Process Regression (GPR) according to Equation (2):

$$g = K(y, y') * A, \quad \text{(Eq. 2)}$$

wherein y is an input vector for GPR, wherein the input vector corresponds to the input matrix x, wherein, however, the value indicating the current refractive status of the person, typically the spherical value for both eyes of the person, is replaced by the ratio R of the axial length divided by the corneal radius data obtained as intermediate prediction data by using the preceding first prediction model 136 according to Equation 1;

y' is a trained active set vectors of the Gaussian Process Regression;

A is a vector of weights for each trained active set vector;

* indicated an inner product calculation; and

K(y, y') is a kernel used for the Gaussian Process Regression, for which purpose that a variety of functions can be used, typically a Rational Quadratic Kernel according to Equation (3):

$$K(y, y') = \sigma_f^2 \left(1 + \frac{\|y - y'\|^2}{2\alpha\sigma_l^2}\right)^{-\alpha} \quad \text{(Eq. 3)}$$

wherein $\sigma_f$, $\sigma_l$, and a are parameters of Rational Quadratic Kernel, all calculated and stored in the training process.

Further, the determining step 214 can comprise a risk consideration step 220, which may be designated for considering the one or more risk factors as comprised by the input matrix x, specifically the value indicating the current refractive status of both parents of the person, typically the spherical value for both eyes of both parents of the person;

the value indicating the first amount of time spent by the person on near vision working; and the value indicating the second amount of time spent outdoors by the person.

Further, the determining step 214 can comprise a myopia treatment consideration step 222, which may be designated for considering the one or more type of myopia treatment as comprised by the input matrix x, specifically a number indicating a type of optical lens selected from a particular contact lens or a particular spectacle lens as the type of myopia treatment to be applied to the person.

In a providing step 224, the data related to the refractive values 112 are provided by using at the output interface 122, specifically for further processing, to the one or more recipients 124 in a fashion as described above in more detail, in particular via the graphical user interface 126.

Figure 3:
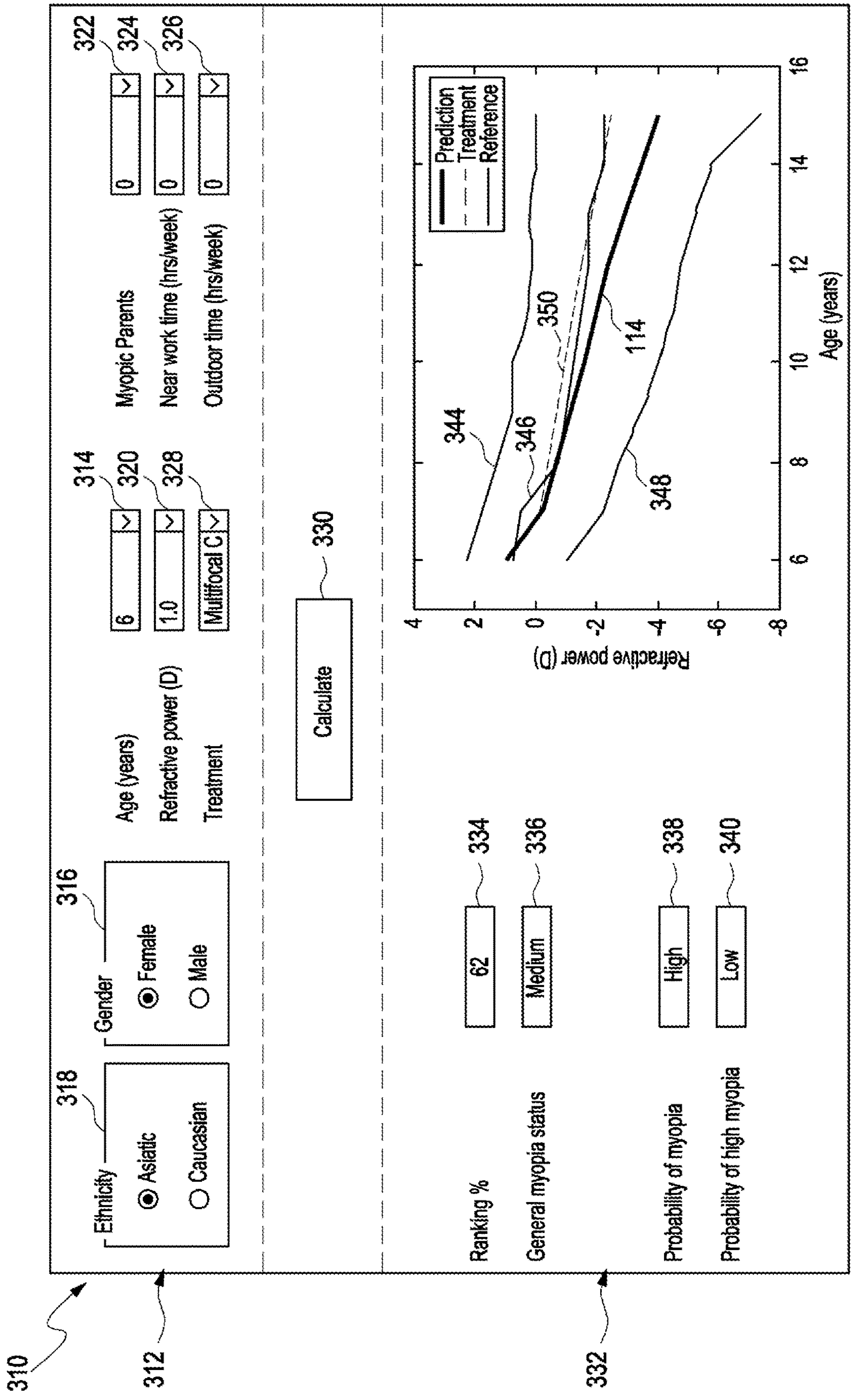
FIG. 3 illustrates an exemplary embodiment of a graphical user interface designated as the input interface and the output interface.

FIG. 3 illustrates an exemplary embodiment of a graphical user interface 310, which is designated here as both the input interface 116 and the output interface 122.

Accordingly, the graphical user interface 310 has a first partition 312 which is designed as the input interface 116 configured to receive the input data 118 related to the person. Here, the input data 118, specifically age 314; gender 316; ethnicity 318; refractive status 320, especially a refractive power; refractive status 322 of at last one parent, especially number of myopic parents; first amount of time 324 spent on near vision working; second amount of time 326 spent outdoors by the person; and a proposed myopia treatment 328 can be adjusted to be entered into the input interface 116.

After a determining button 330 as further comprised by the graphical user interface 310 has been pressed, a second partition 332 of the graphical user interface 310 presents the output data 112 related to the progression 114 of the refractive values of the person, in particular a ranking 334, a general myopia status 336, a risk of myopia 338, and a risk of high myopia 340 delivered, together with a diagram 342 which shows the achieved prediction of the progression 114 of the refractive values of the person as a function of the age 314 of the person, wherein the above-mentioned input data 118, apart from the proposed myopia treatment 328 have been considered. Herein, the ranking 334 may indicate a position of the person compared to other persons at the same age. The general myopia status 336 can be selected from the qualifiers "good," "medium" or "bad," depending on whether the prediction of the progression 114 of the refractive values of the person predicts no myopia ("good"), myopia ("medium"), or high myopia ("bad"). The values for the risk of myopia 338 and the risk of high myopia 340 are determined in a fashion as described above in more detail.

As further depicted in FIG. 3, the diagram 342 as shown in the second partition 332 of the graphical user interface 310, additionally, presents reference curves 344, 346, 348, which represent a $97^{th}$ percentile, a $50^{th}$ percentile and a $3^{rd}$ percentile for a plurality of persons having the same age 314, as well as a modified progression 350 of the refractive values of the person as influenced by the proposed myopia treatment 328 as entered into the input interface 116.

In addition, a study has been performed by the inventors which demonstrates that using machine learning 132 and the large set of input data 118 as acquired for Chinese children, an algorithm for the prediction of spherical power as a function of the age 314 could be developed. In the algorithm which was showing an acceptable performance Support Vector Regression (SVR) and Gaussian Process Regression (GPR) were used as the first and the second prediction model 136, 138, respectively. A performance evaluation demonstrated an acceptable correlation value between the prediction and measured true data, a bias value that was well below 0.25 dpt and limits of agreement that may easily allow distinguishing between children in risk for developing and progressing of myopia.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

110 system
112 output data
114 progression of refractive values of person
116 input interface
118 input data
120 processing device
122 output interface
124 recipient
126 graphical user interface
128 first communication interface
130 second communication interface
132 machine learning algorithm
134 prediction model
136 first prediction model
138 second prediction model
210 computer-implemented method for providing the output data related to the progression of the refractive values of the person
212 receiving step
214 determining step
216 first predicting step
218 second predicting step
220 risk consideration step
222 myopia treatment consideration step
224 providing step
310 graphical user interface
312 first partition
314 age
316 gender
318 ethnicity
320 refractive status of person
322 refractive status of at least one parent of the person
324 first amount of time spent on near vision working
326 second amount of time spent outdoors by the person
328 (type of) myopia treatment
330 determining button
332 second partition
334 ranking
336 general myopia status
338 risk of myopia
340 risk of high myopia
342 diagram
344 $97^{th}$ percentile
346 $50^{th}$ percentile
348 $3^{rd}$ percentile
350 modified progression of refractive values of person

The invention claimed is:

1. A processing device for determining data related to a progression of refractive values of a person, the progression of the refractive values being a forecast of a temporal alteration of the refractive values of at least one eye of the person over a period of time, the processing device being configured to:

receive at least one input file containing data related to the person, the data including:

a refractive status of the person, age, gender, and ethnicity of the person, and at least one risk factor related to the person; and provide at least one output file containing data related to a progression of refractive values of the person determined with at least one machine learning algorithm, wherein the at least one machine learning algorithm is configured to determine the data related to the progression of the refractive values of the person from the data related to the person by deploying the data from the at least one input file in a determining step, wherein the at least one machine learning algorithm includes at least one prediction model for determining a relationship between the data related to the person and the progression of the refractive values of the person, wherein the at least one machine learning algorithm further includes a first prediction model and a second prediction model, wherein, in a first prediction step of the determining step, the first prediction model generates intermediate prediction data including a ratio of an axial length divided by a corneal radius for the person by deploying Support Vector Regression (SVR), wherein the intermediate prediction data are deployed as input for the second prediction model, wherein, in a second prediction step of the determining step, the second prediction model predicts the progression of the refractive values of the person, wherein the second prediction model is a second linear prediction model deploying Gaussian Process Regression (GPR), and wherein a value indicating the refractive status of the person in the at least one input file is replaced by the ratio R of the axial length divided by the corneal radius data in the input of the second prediction model.

2. The processing device according to claim 1, wherein the at least one risk factor is selected from data related to at least one of:

the refractive status of at least one parent of the person; and at least one parameter related to a behavior of the person.

3. The processing device according to claim 2, wherein the at least one parameter related to the behavior of the person is selected from data related to at least one of:

a first amount of time spent by the person on near vision working; and a second amount of time spent outdoors by the person.

4. The processing device according to claim 1, wherein the data related to the person further comprises at least one type of myopia treatment, the at least one type of myopia treatment being selected from an application of at least one of:

an optical lens selected from a contact lens or a spectacle lens, a dose of a drug, and refractive surgery;

and wherein the refractive status is selected from at least one of:

at least one refractive value of at least one eye, at least one biometric value of the at least one eye.

5. The processing device according to claim 1, wherein the first prediction model deploys longitudinal data, wherein the longitudinal data includes a plurality of first pieces of data which are related to a particular person, wherein the second prediction model deploys cross-sectional data, and wherein the cross-sectional data includes at least one second piece of data related to a plurality of different persons.

6. The processing device according to claim 5, wherein a total data input into the at least one machine learning algorithm comprises a first amount of longitudinal data input and a second amount of cross-sectional data input, wherein the first amount is from 30% to 70% and the second amount is from 30% to 70%, wherein the first amount and the second amount add up to 100%.

7. The processing device according to claim 1, wherein the processing device is further configured to determine at least one of:

a ranking of the person compared to a plurality of further persons;

a risk of myopia for the person; and a risk of high myopia for the person.

8. A system for providing data related to a progression of refractive values of a person, the progression of the refractive values being a forecast of a temporal alteration of the refractive values of at least one eye of the person over a period of time, the system comprising:

at least one input interface configured to receive at least one input file containing data related to a person according to claim 1;

a processing device being configured to:

receive the at least one input file containing the data related to the person, including:

a refractive status of the person, age, gender, and ethnicity of the person, and at least one risk factor related to the person; and provide at least one output file comprising data related to a progression of refractive values of the person determined by deploying at least one machine learning algorithm, wherein the at least one machine learning algorithm is configured to determine the data related to the progression of the refractive values of the person from the data related to the person by deploying the data from the at least one input file in a determining step, wherein the at least one machine learning algorithm comprises at least one prediction model for determining a relationship between the data related to the person and the progression of the refractive values of the person; and at least one output interface configured to provide data related to the progression of the refractive values of the person, wherein the at least one machine learning algorithm includes a first prediction model and a second prediction model, wherein, in a first prediction step of the determining step, the first prediction model generates intermediate prediction data containing a ratio of an axial length divided by a corneal radius for the person by deploying Support Vector Regression (SVR), wherein the intermediate prediction data are deployed as input for the second prediction model, wherein, in a second prediction step of the determining step, the second prediction model predicts the progression of the refractive values of the person, and wherein the second prediction model is a second linear prediction model deploying Gaussian Process Regression (GPR).

9. The system according to claim 8, wherein the at least one output interface is further configured to provide at least one of:

at least one percentile referencing for the refractive values, wherein the at least one percentile referencing is provided for population-based data covering a range of ages; and a modified progression of refractive values of the person considering an implementation of the at least one type of myopia treatment.

10. A computer-implemented method for determining data related to a progression of refractive values of a person, the progression of the refractive values being a forecast of a temporal alteration of the refractive values of at least one eye of the person over a period of time, the method comprising:

receiving at least one input file containing data related to a person including:

a refractive status of the person, age, gender, and ethnicity of the person, and at least one risk factor related to the person;

providing at least one output file containing data related to a progression of refractive values of the person determined with at least one machine learning algorithm, wherein the at least one machine learning algorithm is configured to determine the data related to the progression of the refractive values of the person from the data related to the person from the data from the at least one input file in a determining step, wherein the at least one machine learning algorithm includes at least one prediction model for determining a relationship between the data related to the person and the progression of the refractive values of the person, wherein the at least one machine learning algorithm includes a first prediction model and a second prediction model, wherein, in a first prediction step of the determining step, the first prediction model generates intermediate prediction data containing a ratio of an axial length divided by a corneal radius for the person by deploying Support Vector Regression (SVR), wherein the intermediate prediction data are deployed as input for the second prediction model, wherein, in a second prediction step of the determining step, the second prediction model predicts the progression of the refractive values of the person, wherein the second prediction model is a second linear prediction model deploying Gaussian Process Regression (GPR), and wherein a value indicating the refractive status of the person in the at least one input file is replaced by the ratio R of the axial length divided by the corneal radius data in the input of the second prediction model.

11. The method according to claim 10, wherein the first prediction model generates intermediate prediction data, and wherein the intermediate prediction data are deployed as input for the second prediction model.

12. A computer-implemented method for providing data related to a progression of refractive values of a person, the progression of the refractive values being a forecast of a temporal alteration of the refractive values of at least one eye of the person over a period of time, the method comprising:

receiving at least one input file containing data related to the person according to claim 10 from at least one input interface;

determining data related to the progression of the refractive values of the person according to claim 10 with at least one processing device; and providing the data related to the progression of the refractive values of the person with at least one output interface.

13. A computer program comprising instructions which, when the program is executed by a computer, cause the computer to carry out the method according to claim 10.

14. A processing device for determining data related to a progression of refractive values of a person, the progression of the refractive values being a forecast of a temporal alteration of the refractive values of at least one eye of the person over a period of time, the processing device being configured to:

receive at least one input file containing data related to a person, comprising a refractive status of the person, age, gender, and ethnicity of the person, and at least one risk factor related to the person;

provide at least one output file containing data related to a progression of refractive values of the person determined by deploying at least one machine learning algorithm, wherein the at least one machine learning algorithm is configured to determine the data related to the progression of the refractive values of the person from the data related to the person by deploying the data from the at least one input file in a determining step, wherein the at least one machine learning algorithm comprises at least one prediction model for determining a relationship between the data related to the person and the progression of the refractive values of the person, wherein the at least one machine learning algorithm includes a first prediction model and a second prediction model, wherein the first prediction model deploys longitudinal data, wherein the longitudinal data include a plurality of first pieces of data which are related to a particular person;

wherein the second prediction model deploys cross-sectional data, and wherein the cross-sectional data include at least one second piece of data related to a plurality of different persons, and:

wherein a value indicating the refractive status of the person in the at least one input file is replaced by the ratio R of the axial length divided by the corneal radius data in the input of the second prediction model.

15. The processing device according to claim 14, wherein the at least one risk factor is selected from data related to at least one of:

the refractive status of at least one parent of the person;

at least one parameter related to a behavior of the person.

16. The processing device according to claim 14, wherein the at least one parameter related to the behavior of the person is selected from data related to at least one of:

a first amount of time spent by the person on near vision working; and a second amount of time spent outdoors by the person.

17. The processing device according to claim 14, wherein the data related to the person further comprises at least one type of myopia treatment, wherein the at least one type of myopia treatment is selected from an application of at least one of:

an optical lens selected from a contact lens or a spectacle lens, a dose of a drug, and refractive surgery;

and wherein the refractive status is selected from at least one of:

at least one refractive value of at least one eye; and at least one biometric value of the at least one eye.

18. The processing device according to claim 14, wherein a total data input into the at least one machine learning algorithm comprises a first amount of longitudinal data input and a second amount of cross-sectional data input, wherein the first amount is from 30% to 70% and the second amount is from 30% to 70%, and wherein the first amount and the second amount add up to 100%.

19. The processing device according to claim 14, wherein the processing device is further configured to determine at least one of:

a ranking of the person compared to a plurality of further persons;

a risk of myopia for the person; and a risk of high myopia for the person.

20. A system for providing data related to a progression of refractive values of a person, the progression of the refractive values being a forecast of a temporal alteration of the refractive values of at least one eye of the person over a period of time, the system comprising:

at least one input interface configured to receive at least one input file comprising data related to a person according to claim 14;

a processing device being configured to:

receive the at least one input file comprising the data related to the person including:

a refractive status of the person;

age, gender, and ethnicity of the person; and at least one risk factor related to the person;

provide at least one output file comprising data related to a progression of refractive values of the person determined by deploying at least one machine learning algorithm, wherein the at least one machine learning algorithm is configured to determine the data related to the progression of the refractive values of the person from the data related to the person by deploying the data from the at least one input file in a determining step, wherein the at least one machine learning algorithm comprises at least one prediction model for determining a relationship between the data related to the person and the progression of the refractive values of the person; and at least one output interface configured to provide data related to the progression of the refractive values of the person, wherein the at least one machine learning algorithm includes a first prediction model and a second prediction model, wherein the first prediction model deploys longitudinal data, wherein the longitudinal data include a plurality of first pieces of data which are related to a particular person;

wherein the second prediction model deploys cross-sectional data, and wherein the cross-sectional data include at least one second piece of data related to a plurality of different persons.

21. The system according to claim 20, wherein the at least one output interface is further configured to provide at least one of:

at least one percentile referencing for the refractive values, wherein the at least one percentile referencing is provided for population-based data covering a range of ages; and a modified progression of refractive values of the person considering an implementation of the at least one type of myopia treatment.

22. A computer-implemented method for determining data related to a progression of refractive values of a person, the progression of the refractive values being a forecast of a temporal alteration of the refractive values of at least one eye of the person over a period of time, the method comprising:

receiving at least one input file containing data related to a person including:

a refractive status of the person;

age, gender, and ethnicity of the person; and at least one risk factor related to the person;

providing at least one output file containing data related to a progression of refractive values of the person determined by deploying at least one machine learning algorithm, wherein the at least one machine learning algorithm is configured to determine the data related to the progression of the refractive values of the person from the data related to the person from the data from the at least one input file in a determining step, wherein the at least one machine learning algorithm includes at least one prediction model for determining a relationship between the data related to the person and the progression of the refractive values of the person, wherein the at least one machine learning algorithm includes a first prediction model and a second prediction model, wherein the first prediction model deploys longitudinal data, wherein the longitudinal data include a plurality of first pieces of data which are related to a particular person;

wherein the second prediction model deploys cross-sectional data, and wherein the cross-sectional data include at least one second piece of data related to a plurality of different persons, and wherein a value indicating the refractive status of the person in the at least one input file is replaced by the ratio R of the axial length divided by the corneal radius data in the input of the second prediction model.

23. The method according to claim 22, wherein the first prediction model generates intermediate prediction data, and wherein the intermediate prediction data are deployed as input for the second prediction model.

24. A computer-implemented method for providing data related to a progression of refractive values of a person, the progression of the refractive values being a forecast of a temporal alteration of the refractive values of at least one eye of the person over a period of time, the method comprising:

receiving at least one input file containing data related to the person according to claim 22 with least one input interface;

determining data related to a progression of refractive values of a person according to claim 22 with at least one processing device; and providing the data related to the progression of the refractive values of the person with at least one output interface.

25. A computer program comprising instructions which, when the program is executed by a computer, cause the computer to carry out the method according to claim 22.

* * * * *